United States Patent [19]

Harris

[11] Patent Number: 4,744,371

[45] Date of Patent: May 17, 1988

[54] MULTI-CONDUCTOR LEAD ASSEMBLY FOR TEMPORARY USE

[75] Inventor: Donald L. Harris, Key Largo, Fla.

[73] Assignee: Cordis Leads, Inc., Miami, Fla.

[21] Appl. No.: 42,834

[22] Filed: Apr. 27, 1987

[51] Int. Cl.[4] ........................ A61N 1/05; H01R 17/18

[52] U.S. Cl. .................................... 128/786; 439/668; 439/669

[58] Field of Search ................ 439/668, 669; 128/786, 128/781, 642, 419 C, 419 P, 784, 785

[56] References Cited

U.S. PATENT DOCUMENTS

| | | | |
|---|---|---|---|
| 3,291,926 | 12/1966 | Nelson | 439/669 |
| 3,546,657 | 12/1970 | Cook | 439/668 |
| 4,379,462 | 4/1983 | Borkan et al. | 128/786 |
| 4,572,605 | 2/1986 | Hess | 439/669 |
| 4,628,934 | 12/1986 | Pohndorf et al. | 128/786 |
| 4,630,611 | 12/1986 | King | 128/642 |
| 4,644,960 | 2/1987 | Johans | 128/786 |
| 4,667,686 | 5/1987 | Peers-Travarton | 128/785 |
| 4,672,979 | 6/1987 | Pohndorf | 128/419 P |

*Primary Examiner*—Eugene F. Desmond
*Assistant Examiner*—Paula A. Austin
*Attorney, Agent, or Firm*—Henry W. Collins; Thomas R. Vigil

[57] ABSTRACT

The multi-conductor lead assembly comprises a first lead, a second lead and a connector assembly for connecting the leads together. The first lead includes a lead body having a distal end portion with a plurality of electrodes thereon, a proximal end portion with a plurality of sleeve electrodes thereon and a plurality of insulated wire conductors within the lead body and electrically connecting the electrodes on the distal end portion with the sleeve electrodes on the proximal end portion. The second lead includes a lead body with a proximal end, a proximal end portion, a distal end and a distal end portion, and a plurality of insulated wire conductors therein. Each of the one wire conductors has a proximal end and a proximal end portion extending out of the proximal end of the lead body. A sleeve connector is mounted on each wire conductor proximal end portion, and a needle is connected to the proximal ends of the wire conductors. The connector assembly includes a body, the distal end portion of the second lead being received in the body, a plurality of connector clips in the body adapted to receive and to make electrical contact with respective ones of the plurality of sleeve electrodes on the first lead, leafs or blades for electrically connecting each of the wire conductors in the second lead with one of the connector clips, and a closure sleeve for insulating the connection between the connector clips and the sleeve electrodes.

14 Claims, 5 Drawing Sheets

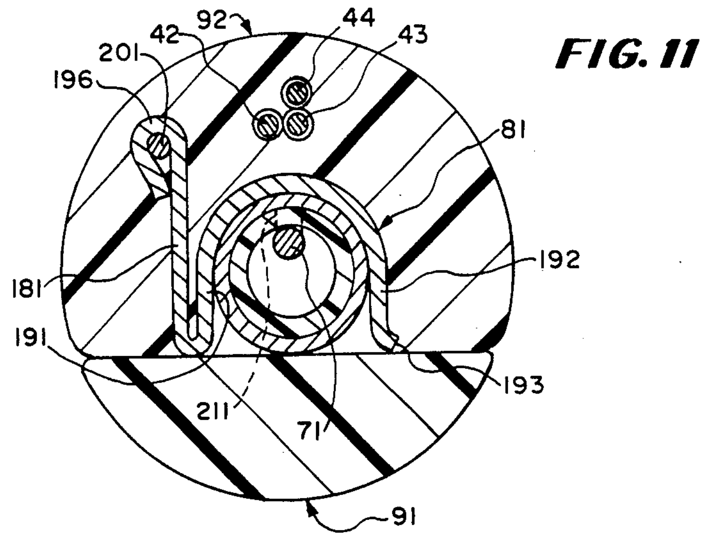
FIG. 11
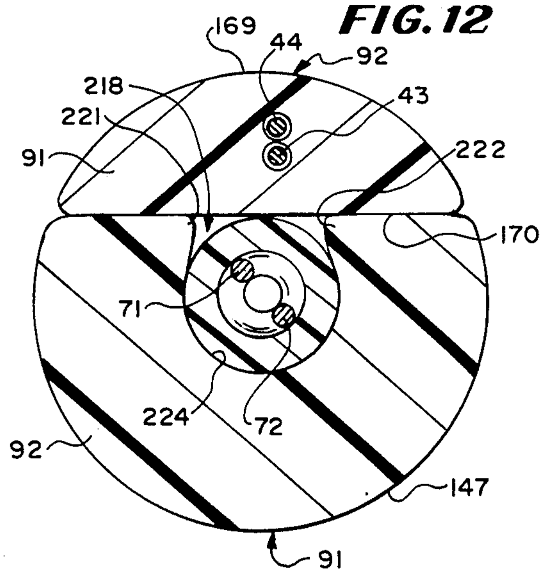
FIG. 12
FIG. 13
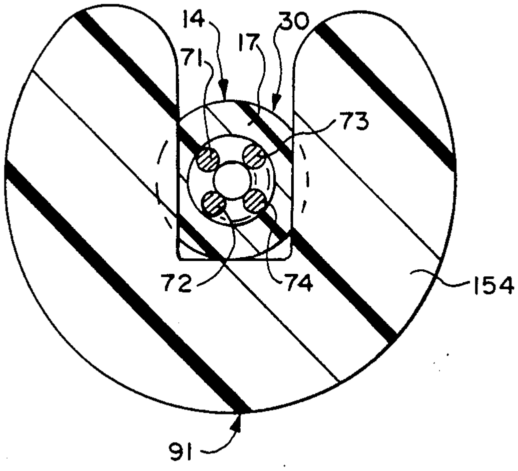

MULTI-CONDUCTOR LEAD ASSEMBLY FOR TEMPORARY USE

BACKGROUND OF THE INVENTION

1. Field of the Invention

The present invention relates to a multi-conductor lead assembly comprising a first lead, a second lead and a connector assembly for connecting the proximal end portion of the first lead to the distal end portion of the second lead. More specifically, the invention relates to a connector assembly which provides a simple and effective structure for temporarily connecting the proximal end of a first lead having a plurality of sleeve electrodes thereon to wire conductors in the second lead in a sealed manner whereby the connector assembly can be inserted in body tissue for temporary use after the distal end of the first lead with electrodes thereon has been implanted in body tissue and electrical tests first have been made, by means of electrical connections to the sleeve electrodes on the proximal end of the first sleeve, on the sensitivity of the implanted ring electrodes.

2. Description of the Prior Art

Heretofore, it has been desirable, in the field of multi-electrode leads which are inserted into the epidural space within the spine and adjacent the spinal cord, to be able to determine which of a number, such as, for example, four, electrodes implanted in the spine are in good conductive contact with the spinal cord. In this respect, it is desirable to be able to test and determine which of the distal electrodes have the best conductive contact with the spinal cord.

One technique which has been proposed for achieving this result is to provide a cathode electrode assembly having four equally spaced in line electrodes along the exterior of a sheath at the distal end of the catheter which are connected to terminals at the proximal end by individually insulated strands of metal wire conductor.

A wire is connected to and extends from each of the terminals to an external terminal each of which is adapted to extend out of body tissue for cutaneous testing during a trial period of stimulation. The wires are cut and removed prior to implantation of the multi-conductor lead assembly and before the terminals at the proximal end of the catheter are connected to a neural stimulator.

Such an assembly is disclosed in the Borkan et al U.S. Pat. No. 4,379,462.

As will be described in greater detail hereinafter, the multi-conductor lead assembly of the present invention, instead of having external terminals which are cut away from a lead, includes two leads, a first lead which has distal electrodes adapted to be implanted within a spine, a second lead with sleeve connectors forming end terminals at the proximal end thereof which are adapted to be withdrawn from tissue for connection to a stimulator, and a connector assembly at the distal end of the second lead into which the proximal end of the first lead is adapted to be inserted and connected after testing is performed, such as with alligator clips connected to electrodes on the proximal end portion of the first lead when it is withdrawn from the tissue for testing purposes. After the testing, the proximal end of the first lead is inserted into the connector assembly and the electrodes thereon are connected to the conductors in the second lead. Then the connector assembly is sealed.

SUMMARY OF THE INVENTION

According to the present invention there is provided a multi-conductor lead assembly comprising:

a first lead including a lead body having a distal end portion with a plurality of electrodes thereon, a proximal end portion with a plurality of sleeve electrodes thereon and a plurality of insulated wire conductors within the lead body and electrically connecting said electrodes on said distal end portion with said sleeve electrodes on said proximal end portion;

a second lead including a lead body having a proximal end, a proximal end portion, a distal end and a distal end portion, and a plurality of insulated wire conductors therein, each of said wire conductors having a proximal end and a proximal end portion extending out of the proximal end of said lead body, a sleeve connector mounted on each wire conductor proximal end portion;

a needle connected to said proximal ends of said wire conductors; and a connector assembly including a body, said distal end portion of said second lead being received in said body, a plurality of connector clips in said body adapted to receive and to make electrical contact with respective ones of said plurality of sleeve electrodes on said first lead, means for electrically connecting each of said wire conductors in said second lead with one of said connector clips, and means for insulating the connection between said connector clips and said sleeve electrodes.

BRIEF DESCRIPTION OF THE DRAWINGS

FIG. 11 is a sectional view through the connector assembly shown in FIG. 10 and is taken along line 11—11 of FIG. 10.

FIG. 12 is a sectional view through the connector assembly shown in FIG. 10 and is taken along line 12—12 of FIG. 10.

FIG. 13 is a sectional view through the connector assembly shown in FIG. 10 and is taken along line 13—13 of FIG. 10.

DESCRIPTION OF THE PREFERRED EMBODIMENT

Figure 1:
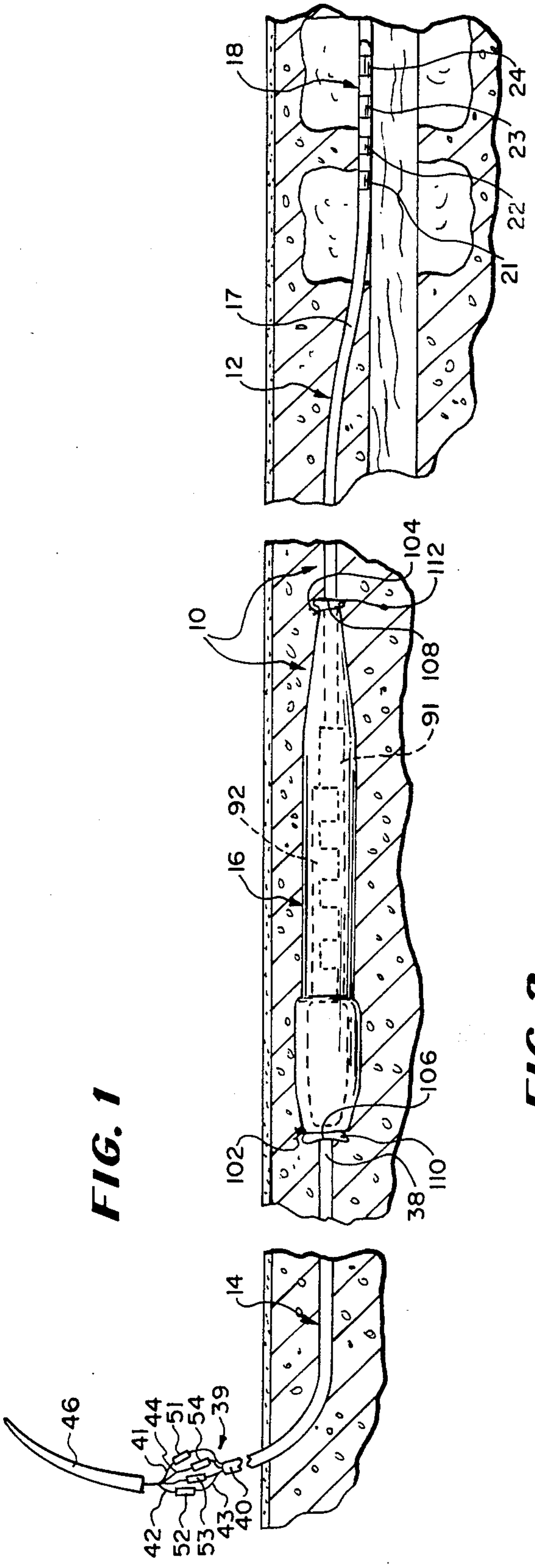
FIG. 1 is a longitudinal plan view with portions broken away of the multi-conductor lead assembly of the present invention and shows a proximal end of a first lead of the assembly inserted in the epidural space of the spine, a proximal end of a second lead of the assembly extending out of body tissue and a connector assembly in which the proximal end of the first lead and the distal end of the second lead are connected together.

In FIG. 1 there is illustrated a multi-conductor lead assembly 10 constructed according to the teachings of the present invention. The assembly 10 includes a first distal lead 12, a second proximal lead 14, and a connector assembly 16 connecting the two leads 12 and 14 together.

FIG. 1 shows the connector assembly 16 of the present invention in its assembled sealed state mounted within body tissue.

The first lead 12 includes a lead body 17 having a distal end portion 18 having four ring electrodes 21–24 (FIG. 1) thereon which are positioned within the epidural space of the spine so that at least one of the ring electrodes 21–24 is in a position to supply electrical current signals to nerve tissue for the purpose of interfering with, and blocking, pain signals. The electrical current path can be between two of the ring electrodes 21–24 or from one electrode 21–24 to an anode connected to the body remotely from the position of the ring electrodes 21–24.

Figure 2:
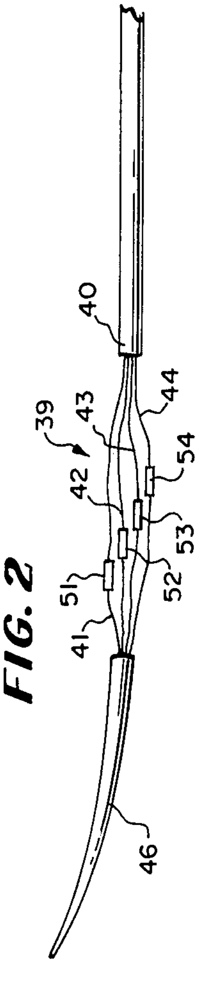
FIG. 2 is a longitudinal plan view of the proximal end portion of the second lead and a needle, connected to four electrical wire conductors which extend out of the proximal end of the second lead and which have sleeve connectors thereon.

A proximal end portion 30 (FIG. 4) of the first lead 12 hidden from view in FIG. 1 has four sleeve electrodes 31–34 (FIG. 2) which are received in the connector assembly 16. The connector assembly 16 is mounted on a distal end portion 38 of the second lead 14.

The second lead 14 has a proximal end portion 39 which includes a proximal end 40 of the lead 14 from which four insulated wire conductors 41–44 extend and are connected to a needle 46. Mounted on each insulated wire conductor 41–44, between the proximal end 40 of the second lead 14 and the needle 46, are four sleeve connectors 51–54.

Figure 3:
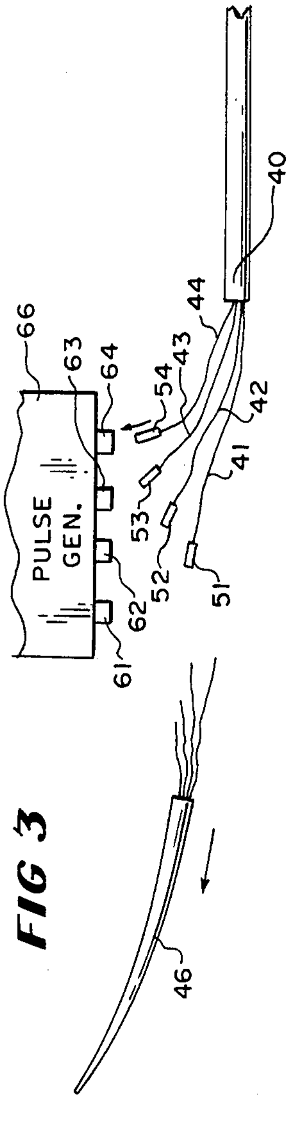
FIG. 3 is a plan view of the needle and end portions of the wire conductors cut away from the sleeve connectors and shows the sleeve connectors juxtoposed to sockets in a pulse generator for receiving same.

As will be described in greater detail hereinafter, once it is determined, such as by testing, which one or ones of the ring electrodes 21–24 in the distal end portion 18 of the first lead 12 is best positioned for supplying stimulating current to nerve tissue, the sleeve connectors 51, 52, 53 or 54 to which a selected ring electrode (or electrodes) 21, 22, 23, or 24 is (or are) connected, are identified (such as by electrical conductivity testing) and the wire conductors 41–44 are cut adjacent the respective sleeve connectors 51–54 as shown in FIG. 3 and the respective, identified, sleeve connectors 51–54 are inserted into a selected one of four sockets 61–64 in an external pulse generator 66.

In this respect, the most distal ring electrode 24 of the electrodes 21–24 is connected to one wire conductor 74 of four wire conductors 71–74 (FIG. 13) in the first lead so as to provide electrical continuity or conductivity from the ring electrode 24, the wire conductor 74 (hidden from view in FIG. 1) to the sleeve electrode 34 (FIG. 4) and then through one connector clip 84 (FIG. 10) of four conductor clips 81–84 (FIG. 10) in the connector assembly 16 to the wire conductor 44 which is connected to the most distal sleeve connector 54 (FIGS. 1 and 2) on the second lead 14. In like manner, a conductive path is provided, respectively, from ring electrode 23 to sleeve connector 53, ring electrode 22 to sleeve connector 52, and ring electrode 21 to sleeve connector 51.

Figure 4:
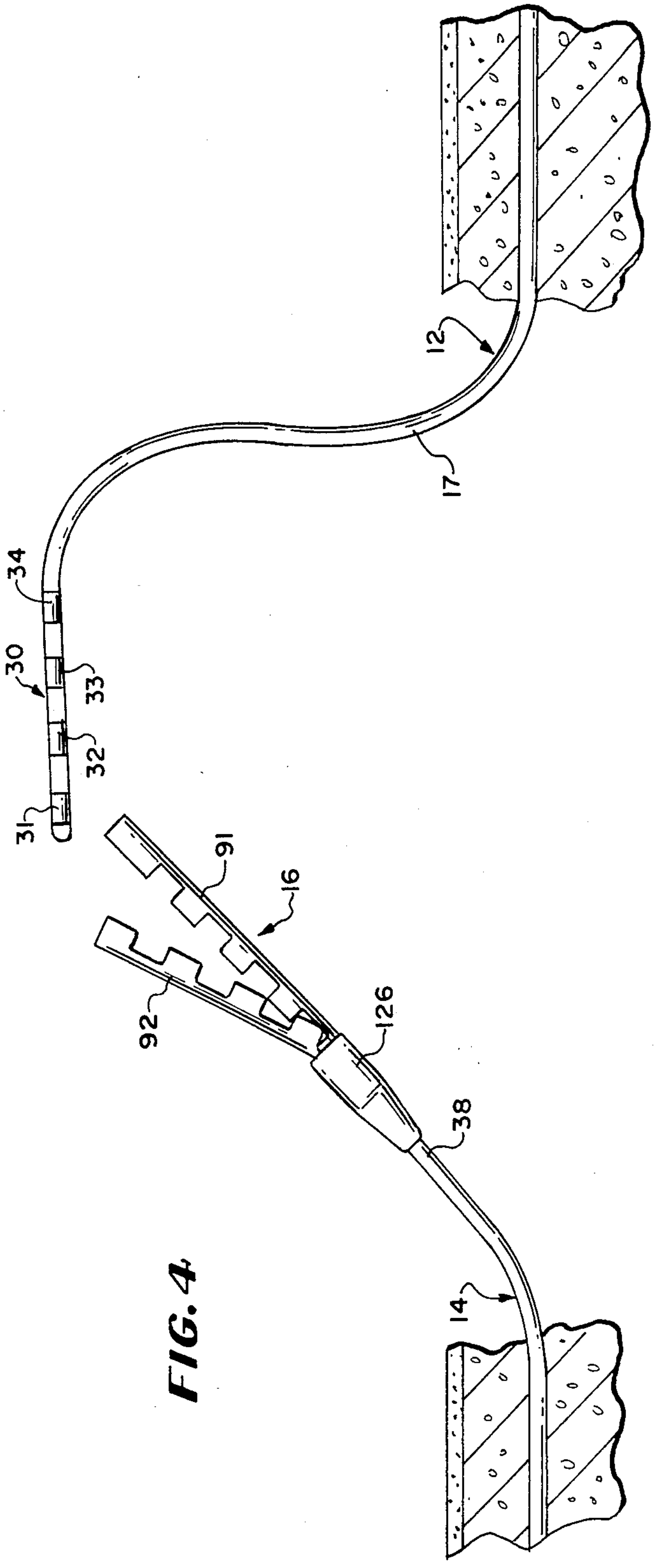
FIG. 4 is an enlarged longitudinal plan view of the multi-conductor lead assembly, shows the proximal end of the first lead drawn out of a body and the connector assembly also drawn out of the body in position to receive the proximal end of the first lead and shows first and second connector legs of the multi-connector assembly which are mounted on the distal end of the second lead and which are spread apart to receive the proximal end of the first lead.

In use, the distal end portion 18 of the first lead 16 is inserted into the epidural space in the spine of a body through a needle and ring electrodes facilitate this method of insertion. Having more than one ring electrode provides the physician with an option to choose electrodes as well as an option to change to another ring electrode if the patient's needs change in the short term. Then, the proximal end portion 30 of the first lead 12 is brought out of the body, as shown in FIG. 4, so that tests can be made by making connections, such as with alligator clips (not shown) between a conductivity sensor (not shown) and the sleeve electrodes 31–34 to determine the sensitivity or effectiveness of contact of each ring electrode 21–24 of the first lead 12 to the spinal cord. In this way, the ring electrode 21–24 which will be connected via sleeve connector 51, 52, 53 or 54, to a selected socket 61–64 in the pulse generator 66 is determined. The electrical testing is performed to check for the position overlying the spinal cord responsible for the pain, to determine stimulus parameters such as rate duration, current needed to diminish pain and to determine which one of the ring electrodes on the lead within the epidural space gives the best results. During the period following surgery and probably over a much longer period, the best results are not always obtained by the same ring electrode.

Then the proximal end 30 of the first lead 12 is inserted between a first longer leg 91 and a second shorter leg 92 (FIG. 4) of the connector assembly 16 and the legs 91, 92 are brought together to establish electrical connection between the wire conductors 41–44 in the second lead 14 and the sleeve electrodes 31–34 on the proximal end portion 30 of the first lead 12.

Figure 5:
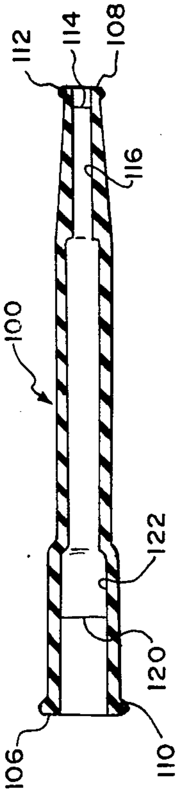
FIG. 5 is a longitudinal sectional view of a closure sleeve which is received on the proximal end of the first lead prior to the insertion of the proximal end of the first lead between the connector legs at the distal end of the second lead after which the closure sleeve is moved over the multi-electrode connector assembly for facilitating a sealed closure over and about the connector legs by the tying of sutures around and adjacent each end of the closure sleeve.

Of course, before this is done a closure sleeve 100 (FIG. 5) is inserted over the proximal end portion 30 of the first lead 12 and far enough up on the lead 12 so that the proximal end portion 30 of the first lead 12 can be inserted between the legs 91 and 92 of the connector assembly 16. Then, after the legs 91 and 92 are brought together about the proximal end portion 30 of this first lead 12, the closure sleeve 100 is slid back over the connector assembly 16 and sutures 102 and 104 (FIG. 1) are tied around each end 106 and 108 of the sleeve 100 to fix the closure sleeve 100 over the connector assembly 16 and to seal the connections in the connector assembly 16 from body fluids. This is assisted by providing a bead 110 at the end 106 of the sleeve 100 and a bead 112 at the end 108 of the sleeve 100 for keeping each suture 102, 104 (FIG. 1) on the sleeve 100 so it will not come off the respective end of the sleeve 100.

Additionally, an annular rib 114 can be provided within a lumen 116 of the sleeve 100 adjacent the end 108 which is received over the first lead 12 and a similar annular rib 120 can be provided in a larger lumen 122 of the sleeve 100 adjacent the end 106 of the sleeve 100 which is received over a cylindrical body 126 of the connector assembly 16 for providing an internal seal between the interior of the sleeve and the body 126 and the first lead 12.

Figure 10:
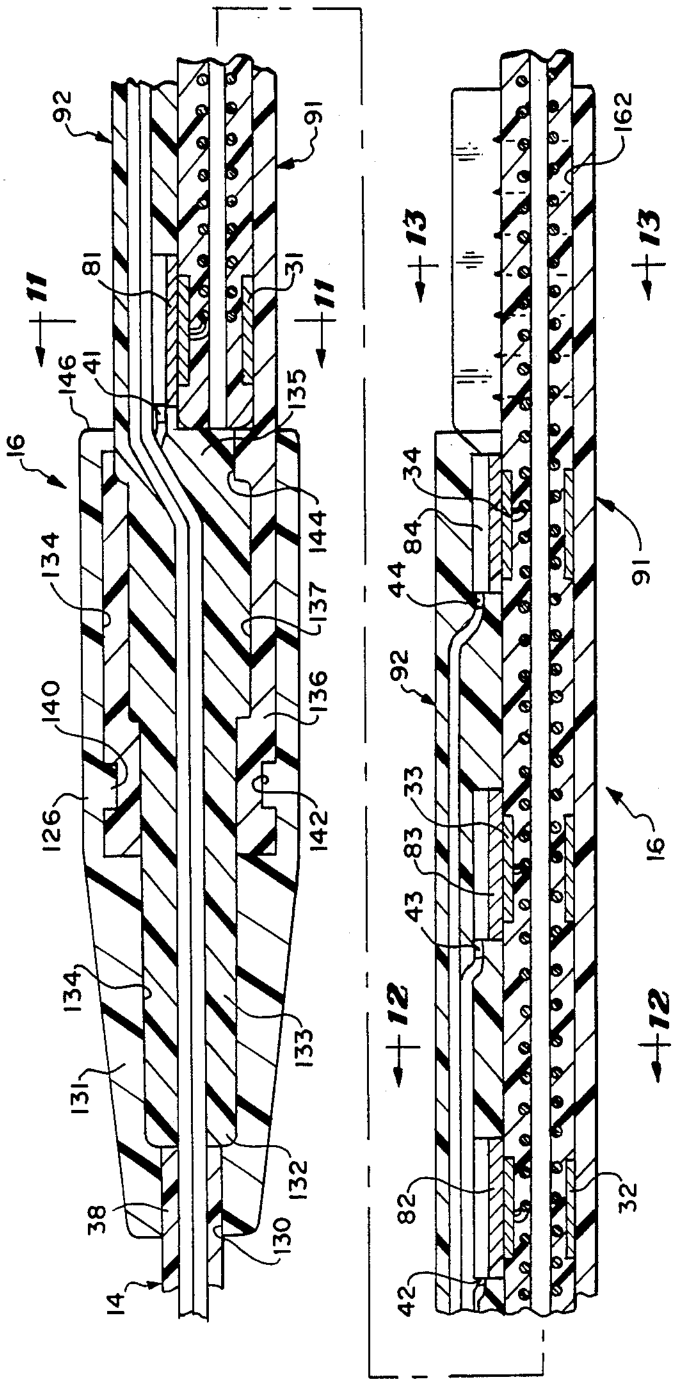
FIG. 10 is an enlarged longitudinal sectional view through the closed multi-electrical connector assembly shown in FIG. 8.

As best shown in FIG. 10, the connector assembly 16 of the present invention has the distal end portion 38 of the second lead 14 received in a bore 130 in a tapered proximal end portion 131 of the body 126. The insulated wire conductors 41–44 in the second lead 14 extend from the proximal end portion 38 into a proximal end 132 of a finger portion 133 received in a stepped cavity 134 in the body 126 to, and longitudinally within, the upper shorter leg 92 which is integral with a distal end 135 of the finger portion 133.

The finger portion 133 and the upper second leg 92 is preferably integral therewith and such structure is preferably made of an elastomeric material.

Within the stepped cavity 134 in the body portion 126, is positioned a cylindrical sleeve 136 made of a more rigid plastic material, such as a thermoplastic material. This sleeve 136 has an at least partially annular hollow 137 which receives an at least partially annular boss 138 of the finger portion 132 thereby to prevent relative longitudinal movement between the finger portion 133 and the cylindrical sleeve 136.

Also, as shown in FIG. 10, the body portion 126 has, within the cavity 134, an annular rib 140 which is received in an annular groove 142 on the outer surface of the cylindrical sleeve 136 to prevent relative longitudinal movement between the body 126 and the cylindrical sleeve 136.

The first leg 91 is integral with and extends axially outwardly from the cylindrical sleeve 136 adjacent a partially annular rib 144 at a distal end 146 of the sleeve 136. The first leg 91 is made of a hard, stiff, rigid, thermoplastic material.

Figure 6:
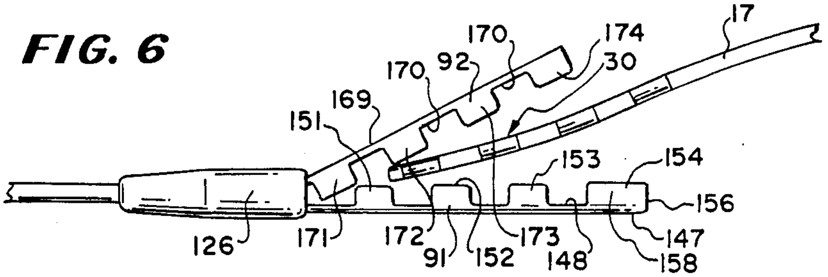
FIG. 6 is a fragmentary longitudinal view showing the proximal end of the first lead positioned between the connector legs of the connector assembly mounted at the distal end of the second lead.
Figure 7:
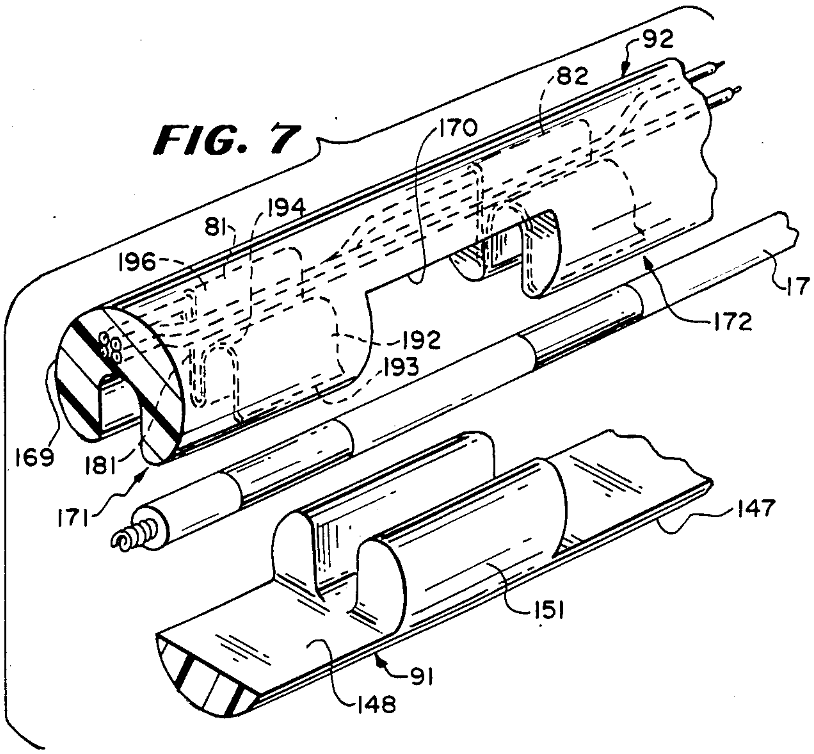
FIG. 7 is an enlarged perspective view of a section of the proximal end portion of the first lead above a saddle formation on the first leg and below two saddle formations, each containing an electrical connector clip on the second leg above the proximal end portion of the first lead and above the first leg.
Figure 8:
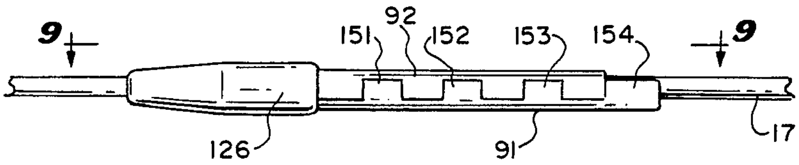
FIG. 8 is a longitudinal plan view of the first and second legs of the connector assembly brought together about the proximal end portion of said first lead.

As best shown in FIGS. 6 and 7, the first leg 91 has a partially cylindrical outer surface 147 and a flat inner or upper surface 148 with four saddle formations 151–154 extending upwardly from the flat surface 148. The saddle formations 151, 152, and 153 are adapted to receive segments of the proximal end portion 30 of the first lead 12 between the spaced apart sleeve electrodes 31–34 thereon.

Figure 9:
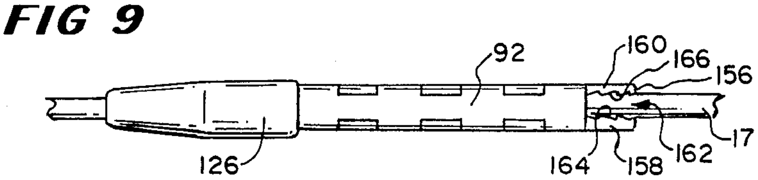
FIG. 9 is a longitudinal plan view taken along line 9—9 of FIG. 8 and shows a gripping formation on the distal end portion of the first leg of the connector assembly for gripping the proximal end portion of the first lead.

The distal saddle formation 154, located at a distal end 156 of the first leg 91, includes a first jaw 158 (FIG. 9) and a second jaw 160 (FIG. 9) separated by a slot 162 (FIGS. 9 and 10). The sides of the jaws 158, 160, facing each other on each side of the slot 162 (FIGS. 9 and 10) have teeth 164, 166 (FIG. 9) thereon for gripping the proximal end portion 30 of the first lead 12, just distal of the proximal end portion 30 thereof, to assist in holding the proximal end portion 30 of the first lead 12 on and between the legs 91 and 92 of the connector assembly 16.

The second leg 92, made of a flexible elastomeric material, can be flexed and raised above the stiff first leg 91, much like an alligator's jaw, as shown in FIGS. 4 and 6.

The second leg 92 has a partially cylindrical outer surface 169 and a flat surface 170 facing inwardly and downwardly. Extending downwardly from the flat surface 170 are four saddle formations 171–174 (FIG. 6). Mounted within each of the saddle formations 171–174 is one of the spring connector clips 81, 82, 83 or 84 each of which is generally U-shaped in cross-section and includes a third connector leaf or blade 181, 182, 183 or 184, extending upwardly from one leg portion, e.g., leg portion 191 of the clip 81. Since each of the connector clips 81–84 is identical, only the connector clip 81 will be described in detail below.

As shown in FIGS. 7 and 11, the connector clip 81 has a second leg portion 192 having a free edge 193, a bight portion 194, and the first leg portion 191 which has the connector leaf or blade 181 integral therewith and extending upwardly generally parallel to the first and second leg portions 191 and 192 to a rounded curled over or bent end portion 196. An uninsulated end portion 201 (FIG. 11) of the wire conductor 41 is received in the curled over or bent end portion 196 of the leaf 181 which is crimped over the uninsulated end portion 201 to make a mechanical and electrical connection therewith.

The inside width of each U-shaped connector clip 81–84 is less than the outer diameter of each of the sleeve electrodes 31–34 so that an interference friction fit is made between each aligned clip 81–84 and sleeve electrode 31–34 when the second leg 92 is brought down over the proximal end portion 30 of the first lead 12 and against the first leg 91.

This is done, of course, after the sleeve electrodes 31–34 are aligned and in registry with the U-shaped, spring connector clips 81–84 with the uninsulated segments of the first lead 12 therebetween aligned with the saddle formations 151, 152, and 153 of the first leg 91.

It will be appreciated from the foregoing description of the construction of the U-shaped connector clip 181 that uninsulated wire conductor end portions of the other wire conductors 32, 33 and 34 are connected in a similar manner, as the end portion 201, to the respective U-shaped, spring connector clips 82, 83 and 84.

As shown in FIGS. 7 and 10–13, the insulated wire condcutors 41–44 are embedded in and extend longitudinally in the elastomeric second leg 92 with the uninsulated end, e.g. end 201 of wire conductor 47, of each insulated conductor 41–44 branching off for connection to one of the connector clips 81–84.

As shown schematically in FIG. 13, the first lead 12 has the four wire conductors 71–74 therein which can be straight or coiled (preferably coiled) within the lead body 17 and which, although shown uninsulated, are actually insulated.

Shown schematically in FIG. 11 is the wire conductor 71 in the proximal end portion 30 of the first lead 12 which has an uninsulated end portion 211 that is brought out of the lead body 17 to make connection with the sleeve electrode 31. Likewise, the proximal end portions of wire conductors 72, 73 and 74 are connected to sleeve electrodes 32, 33 and 34.

FIG. 12 is a sectional view through a segment of the proximal end portion 30 of the first lead 12 received in the saddle formation 152 of the first leg 91. As shown, the saddle formation 152 can have a slot 218 which is narrower at the top thereof between jaw portions 221 and 222 thereof than at a bight 224 thereof so that a segment of the proximal end portion 30 of the first lead 12 is snapped fittingly received in the saddle formation 151, 152 or 153.

FIG. 13 is a sectional view through the distal saddle formation 154 at the distal end 156 of the first leg 91 and shows the teeth 164 and 166 in gripping engagement with the lead body 17 of the first lead 12.

In use, as described above, after the distal end portion 18 of the first lead 12 is inserted in the epidural space within the spine of a body, the sensitivity or conductive path between each of the ring electrodes 21, 22, 23 and 24 and adjacent nerve tissues is determined by performing conductivity tests, such as by making selective connections to the sleeve electrodes 31, 32, 33 and 34 on the proximal end portion 30 of the first lead 12 which is withdrawn from the body for this purpose.

Once the sensitivity or threshold level of each of the ring electrodes 21, 22, 23 and 24 is determined, the closure sleeve 100 is inserted over the proximal end portion 30 of the first lead 12. Then the proximal end portion 30 of the first lead 12 is placed on the first leg 91 with the sleeve electrodes 31–34 aligned with the spring connector clips 81-84 in the saddle formations 171–174 of the second leg 92. Then the second leg 92 is brought down on top of the first leg 91 and each of the saddle formations 171–174 is squeezed over respective ones of the sleeve electrodes 31, 32, 33 and 34.

Then the closure sleeve 100 is moved over the closed legs 91 and 92 and the sutures 102 and 104 are tied in place to seal the closure sleeve 100 about the body 26 and legs 91 and 92 of the connector assembly 16 and particularly about the first and second legs 91 and 92 with the proximal end portion 30 of the first lead 12 clamped therebetween.

The sutures 102 and 104 are tied about the respective ends 106 and 108 of the closure sleeve 100 to seal the connector assembly 16, after which the needle 46 is pulled out to pull the encased connector assembly 16 into body tissue to the position shown in FIG. 1.

Then, the wire conductors 41–44 are cut against the proximal end of the respective sleeve connectors 51–54.

Next, based upon the previous tests made, the sleeve connectors 51–54 are inserted into selected sockets 61–64, in the external pulse generator 66 and the neural stimulating lead assembly 10 is ready for use. This assembly 10 is ideal for short term use, at the most three weeks, the connector assembly 16 and its lead 14 should be removed and replaced with a relatively more permanent assembly as disclosed in copending Application Ser. No. 042,677, filed on Apr. 27, 1987 for: LEAD ASSEMBLY WITH SELECTABLE ELECTRODE CONNECTION can be employed.

From the foregoing description, it will be apparent that the multi-conductor neural stimulating assembly 10 of the present invention and particularly the connector assembly 16 thereof have a number of advantages some of which have been described above and others of which are inherent in the invention. In particular, the simple and easy way of connecting the proximal end portion 30 of the first lead 12 to the connector assembly 16 and the sealing of same enables testing of the sensitivity or threshold level of each ring electrode 21, 22, 23 and 24 adjacent nerve tissue in the epidural space within the spine of the body prior to connection of the lead 12 to the lead 14.

Additionally from the foregoing description, it will be understood that modifications can be made to the neural stimulating lead assembly 10 of the present invention and the connector assembly 16 thereof without departing from the teachings of the present invention. Accordingly, the scope of the invention is only to be limited as necessitated by the accompanying claims.

I claim:

1. A multi-conductor lead assembly comprising:

a first lead including a lead body having a distal end portion with a plurality of electrodes thereon, a proximal end portion with a plurality of sleeve electrodes and a plurality of insulated wire conductors within the lead body and electrically connecting said electrodes on said distal end portion with said sleeve electrodes on said proximal end portion;

a second lead including a lead body having a proximal end, a proximal end portion, a distal end and a distal end portion, and a plurality of insulated wire conductors therein, each of said wire conductors having a proximal end and a proximal end portion extending out of the proximal end of said lead body, a sleeve connector mounted on each wire conductor proximal end portion;

a needle connected to said proximal ends of said wire conductors; and a connector assembly including a body, said distal end portion of said second lead being received in said body, a plurality of connector clips in said body adapted to receive and to make electrical contact with respective ones of said plurality of sleeve electrodes on said first lead, means for electrically connecting each of said wire conductors in said second lead with one of said connector clips, and means for insulating the connection between said connector clips and said sleeve electrodes.

2. The lead assembly of claim 1 wherein said body of said connector assembly includes a first rigid leg and a second movable leg, said proximal end portion of said first lead being received between said legs.

3. The assembly of claim 2 wherein said connector clips are mounted in said second leg.

4. The assembly of claim 2 wherein said second leg is made of a flexible material, said body including an annular housing and one end of each of said legs is received in said annular housing with said second leg being made of flexible material and being bendable adjacent said annular housing.

5. The lead assembly of claim 4 wherein said distal end portion of said second lead extends into one end of said annular housing, said plurality of insulated wire conductors in said distal end portion extending into a proximal end of said second leg received inside said annular housing and into said second leg extending from said housing, each conductor extending to and making electrical contact with one of said connector clips.

6. The lead assembly of claim 4 wherein said annular housing is generally tubular and said second leg has an inner end which includes a finger portion which is received inside said tubular housing and said first leg has a proximal end portion which is received in said tubular housing and which is at least partially annular and has said finger portion of said second leg received therein.

7. The assembly of claim 2 wherein said second leg has generally U-shaped saddle formations thereon equal in number to said plurality of wire conductors and to said plurality of clip connectors, and one of said connector clips is mounted within each one of said generally U-shaped saddle formations.

8. The assembly of claim 1 wherein said first rigid leg has a plurality of generally U-shaped saddle formations, one less than the U-shaped saddle formations in said second leg, said U-shaped saddle formations on said first rigid leg being adapted to receive segments of said proximal end portion of said second lead located in the areas between said sleeve electrodes on said proximal end portion of said first lead and between said U-shaped connector clips mounted in U-shaped saddle formations of said second leg.

9. The lead assembly of claim 2 wherein said first leg has a U-shaped formation adjacent the distal end thereof, said U-shaped formation being defined by a bight portion and first and second leg portions, said first and second leg portions having means thereon for engaging said proximal end portion of said first lead for preventing longitudinal movement of said first lead relative to said second leg.

10. The lead assembly of claim 9 wherein said means for engaging the proximal end of said first lead comprises teeth on the inner surface of each of said leg portions.

11. The lead assembly of claim 4 wherein said insulating means of said connector assembly includes a tubular closure member which is initially received on said first lead and after said proximal end portion of said first lead is received between said first and second legs, said tubular closure member is moved over said legs with said proximal end portion of said first lead clamped therebetween and over said annular housing.

12. The lead assembly of claim 11 wherein said insulating means includes tie means tied around each end of said tubular closure member when it is positioned about said body comprising said housing and said first and second legs with said proximal end portion of said first lead positioned between the legs.

13. The lead assembly of claim 12 wherein said tubular closure member has an exterior annular rib at each end to prevent said tie means from coming off of said tubular closure member.

14. The lead assembly of claim 12 wherein said tubular closure member has an internal annular rib adjacent each end thereof for establishing seals with, respectively, said housing and said lead body of said first lead.

* * * * *

UNITED STATES PATENT AND TRADEMARK OFFICE
CERTIFICATE OF CORRECTION

PATENT NO. : 4,744,371

DATED : May 17, 1988

INVENTOR(S) : Donald L. Harris

It is certified that error appears in the above-identified patent and that said Letters Patent is hereby corrected as shown below:

Column 9, Line 4, "1" should be --7--.

Signed and Sealed this

Twelfth Day of February, 1991

*Attest:*

HARRY F. MANBECK, JR.

*Attesting Officer*

*Commissioner of Patents and Trademarks*